(12) United States Patent
Cali et al.

(10) Patent No.: US 8,439,860 B2
(45) Date of Patent: May 14, 2013

(54) OXYGEN-PRODUCING BANDAGE WITH RELEASABLE OXYGEN SOURCE

(75) Inventors: Lawrence J. Cali, East Falmouth, MA (US); Srinivasan Sarangapani, Walpole, MA (US); Jeffrey C. DiTullio, Lynnfield, MA (US)

(73) Assignee: Neogenix, LLC, Ft. Lauderdale, FL (US)

( * ) Notice: Subject to any disclaimer, the term of this patent is extended or adjusted under 35 U.S.C. 154(b) by 0 days.

(21) Appl. No.: 12/709,902

(22) Filed: Feb. 22, 2010

(65) Prior Publication Data

US 2010/0217177 A1    Aug. 26, 2010

Related U.S. Application Data

(60) Provisional application No. 61/154,786, filed on Feb. 24, 2009.

(51) Int. Cl.
*A61M 37/00* (2006.01)
*A61F 13/00* (2006.01)

(52) U.S. Cl.
USPC ............... 604/23; 604/26; 604/304; 604/307

(58) Field of Classification Search ............ 604/23, 604/24, 25, 26, 304, 307, 308
See application file for complete search history.

(56) References Cited

U.S. PATENT DOCUMENTS

| | | | |
|---|---|---|---|
| 4,328,799 A | 5/1982 | LoPiano | |
| 4,539,086 A | 9/1985 | Fujita et al. | |
| 4,608,041 A | 8/1986 | Nielsen | |
| 5,336,209 A | 8/1994 | Porzilli | |
| 5,449,340 A | 9/1995 | Tollini | |
| 5,578,022 A | 11/1996 | Scherson et al. | |
| 5,607,388 A | 3/1997 | Ewall | |
| 5,702,356 A * | 12/1997 | Hathman | 602/41 |
| 5,788,682 A | 8/1998 | Maget | |
| 5,792,090 A | 8/1998 | Ladin | |
| 5,855,570 A | 1/1999 | Scherson et al. | |
| 7,304,201 B2 * | 12/2007 | Holloway et al. | 602/41 |
| 7,429,252 B2 | 9/2008 | Sarangapani | |
| 2003/0212357 A1 | 11/2003 | Pace | |
| 2006/0287632 A1 * | 12/2006 | Sarangapani | 604/304 |
| 2007/0282236 A1 * | 12/2007 | LaGreca | 602/43 |
| 2008/0269658 A1 | 10/2008 | Vinton et al. | |
| 2009/0005722 A1 | 1/2009 | Jennlngs-Spring | |

FOREIGN PATENT DOCUMENTS

| | | |
|---|---|---|
| EP | 0 942 768 B1 | 11/2002 |
| WO | WO 00-07653 A1 | 2/2000 |
| WO | WO 2006/122169 A2 | 11/2006 |
| WO | WO 2007/070110 A2 | 6/2007 |

OTHER PUBLICATIONS

International Search Report and Written Opinion from PCT/US2010/025055, date of mailing Oct. 6, 2010, 11 pages.

(Continued)

*Primary Examiner* — Bhisma Mehta
(74) *Attorney, Agent, or Firm* — Hamilton, Brook, Smith & Reynolds, P.C.

(57) ABSTRACT

A device for delivering oxygen to a wound or injury includes a bandage, which includes a base defining an opening, a cover, and a locking mechanism for releasably securing the cover to the base. An oxygen source is in fluid communication with the cover, whereby oxygen is delivered to the opening in the base.

19 Claims, 6 Drawing Sheets

OTHER PUBLICATIONS

International Preliminary Report on Patentability issued Aug. 30, 2011 from International Application No. PCT/US2010/025055 filed Feb. 24, 2009.

International Supplementary European Search Report from corresponding International European Patent Application No. 10746704.5 dated Oct. 10, 2012.

* cited by examiner

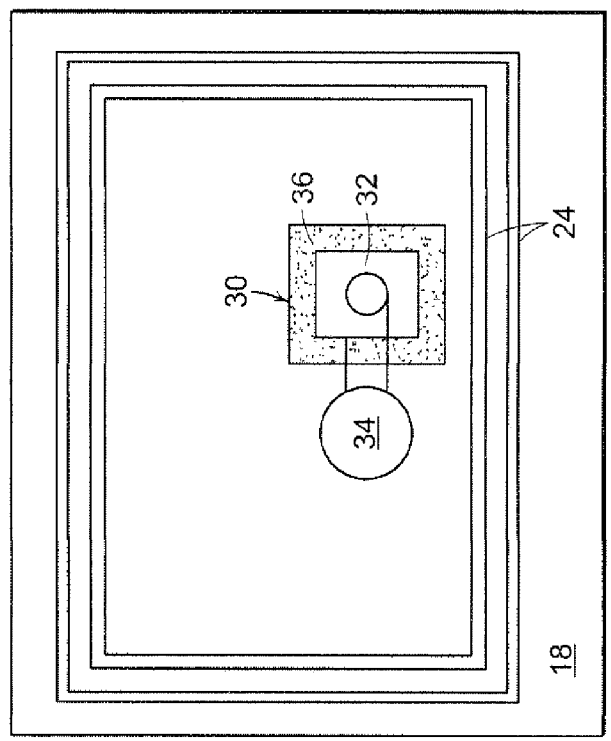
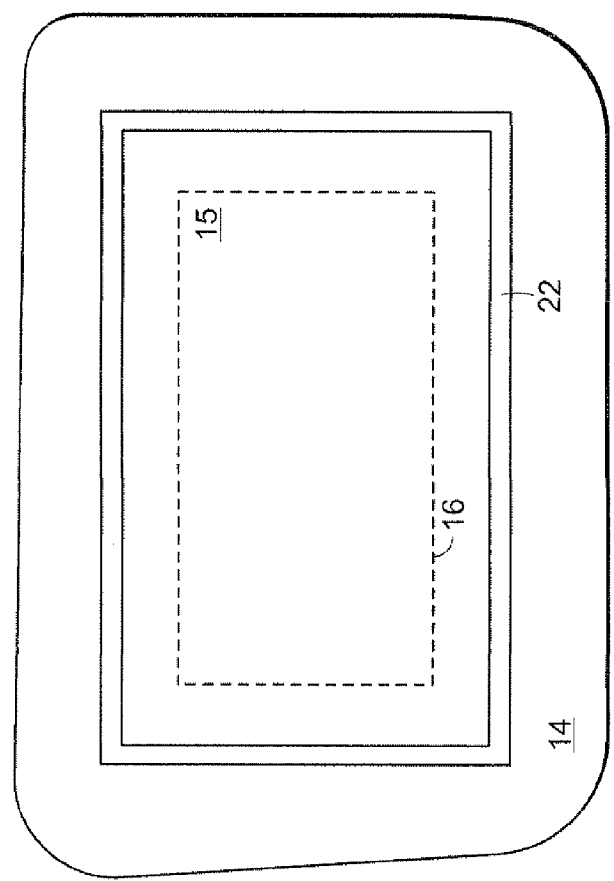
FIG. 2B
FIG. 2A

OXYGEN-PRODUCING BANDAGE WITH RELEASABLE OXYGEN SOURCE

RELATED APPLICATION

This application claims the benefit of U.S. Provisional Application No. 61/154,786 filed on Feb. 24, 2009.

The entire teachings of the above application are incorporated herein by reference.

BACKGROUND OF THE INVENTION

Oxygen is often employed to healing of the wounds (e.g., ulcers, abrasions, cuts, sores, etc.). Topical oxygen therapy calls for applying oxygen directly to an open wound. The oxygen dissolves in tissue fluids and improves the oxygen content of the intercellular fluids. Injuries and disorders which may be treated with topical oxygen include osteomyelitis, tendon and cartilage repair, sprains, fractures, burns and scalds, necrotizing fasciitis, pyoderma gangrenosum, refractory ulcers, diabetic foot ulcers and decubitus ulcers (bed sores) as well as cuts, abrasions, and surgically induced wounds or incisions.

There have been several attempts to promote wound healing by supplying oxygen to a wound or regulating the oxygen concentration in the vicinity of a wound.

Oxygen chambers apply oxygen either systemically or topically. In the former, the patient breaths high pressure pure oxygen, and in the latter the entire affected limb is placed in a sealed chamber that features controlled pressure sealing and automatic oxygen regulation control. Not only are such oxygen chambers expensive and difficult to sterilize, they are also cumbersome in that the chamber must be hooked up to an external oxygen tank, limiting the patient's mobility. In addition, in the systemic method of oxygen application, the various organs of the body may be unnecessarily subjected to high levels of oxygen. Such high levels of oxygen present risks of vasoconstriction, toxicity and tissue destruction.

Devices in which oxygen is produced electrochemically and transported across an ion conductive membrane typically depend upon water, which has a relatively high vapor pressure and will evaporate. As water in the membrane evaporates, the membrane loses its ability to effectively conduct ions. Thus, over the course of several days, membranes used in such devices tend to lose their ability to transportions and must either be replaced or re-hydrated. Further, attempting to keep the membrane hydrated can result in complications. For example, the inclusion of a water source to keep the membrane moist can make the device cumbersome, mitigating one of the key benefits of such a device. In addition, the close proximity of water to open wounds causes susceptibility to microbial infection.

Self-contained, portable oxygen concentrating devices, such as the one taught in U.S. Pat. No. 7,429,252, employ an ion conducting membrane that does not need to be constantly humidified to maintain conductivity. The oxygen concentrator in such devices is capable of operating for months, but due to limitations of the primary battery, the device must be replaced after a single use.

Many wound locations, e.g., foot, heel, lower ankle etc., call for devices that are thin and flexible, so that they will not interfere with shoes and such outerwear that are part of an ambulatory patient. Thick end plates (for electrical connection and air and oxygen delivery) often used in electrochemical oxygen generating devices generally do not fulfill this requirement.

Bandages and dressings placed over wounds absorb exudate from the environment and need to be disposed of anywhere between 1-7 days after application, depending on the level of exudate generation. In oxygen producing devices, such as those as described above, the dressing then needs to be disposed, since the absorbent dressing becomes saturated with the wound exudate. The oxygen producing device is expensive to make and disposing of the entire dressing, along with the oxygen-producing device is both economically and environmentally undesirable.

Therefore, there is a need for an oxygen delivery device that can reduce or minimize the aforementioned problems.

SUMMARY OF THE INVENTION

The present invention generally is directed to a device for delivering oxygen to a wound or injury and to a method of treatment of a wound with oxygen gas by use of the device.

The device for delivering oxygen to a wound or injury includes a bandage, which includes a base defining an opening, a cover, and a locking mechanism for releasably securing the cover to the base. An oxygen source is in fluid communication with the cover, whereby oxygen is delivered to the opening in the base.

In another embodiment, the invention is a method for treating a wound with oxygen gas. The method includes applying a bandage to a wound site. The bandage includes a base defining an opening, a cover and a locking mechanism for releasably securing the cover to the base. An oxygen source that is in fluid communication with the cover is actuated, and oxygen gas is delivered from the oxygen source through the cover to the opening in the base thereby treating the wound with oxygen gas.

The present invention relates to a process to make oxygen producing devices for wound care application. The present invention overcomes at least some of the inherent problems in the construction and operation of the portable, self-contained devices for the topical application of oxygen to promote wound healing described in U.S. Pat. Nos. 5,578,022 and 5,788,682.

The present invention has many advantages. For example, the removable cover of the bandage holds an oxygen source, such as the EPIFLO® transdermal continuous oxygen therapy device, which includes a membrane-electrode assembly, a power supply, and control electronics. The components of the oxygen source are sealed into the removable cover with openings only to allow air entry and oxygen exit. In the case where a battery powers the oxygen source, an exhausted battery or oxygen source can easily be replaced with a fresh one without the need to replace the complete bandage or the complete device. In this way, the patient's wound does not experience the stress associated with removing the adhesive part of the bandage each time the battery or the oxygen source is replaced.

Another benefit of a bandage cover that is releasably secured to the bandage base is that a doctor can easily remove the cover including the oxygen source at any point to inspect the patient's wound or refresh absorbents used in the bandage. In this case, since the oxygen source still has battery life remaining, it can be returned to the bandage, thereby providing cost savings over conventional designs, where the bandage and the oxygen source are an integral unit. An additional benefit is that the patient can remove the cover, including the oxygen source, before bathing and replace it afterwards. A watertight blank can be substituted for the cover while the patient is bathing thus keeping the wound dry.

Also, the bandage of the oxygen delivery device of the invention can be placed directly over a conventional bandage of the doctor's choice. The adhesive layer on the base of the bandage will hold the bandage in place on top of the conventional bandage.

A cover releasably secured to a bandage base can also be applied to bandages that do not provide an oxygen source. The removable cover and the base of the bandage can contain absorbent that can then be easily changed. Doctors can remove the cover to inspect the wound without having to remove the adhesive part of the bandage. The cover can be filled with medicines (including oxygen) intended to assist with wound healing. The bandage cover and the medicines can easily be replaced when necessary. Finally, the bandage can be fitted with a watertight blank when the patient wishes to bathe in order to keep the wound dry.

BRIEF DESCRIPTION OF THE DRAWINGS

FIG. 2A is a top view of a bandage base of one embodiment of an oxygen delivery device of the invention.

FIG. 2B is a bottom view of a bandage cover of the oxygen delivery device of FIG. 1A.

DETAILED DESCRIPTION OF THE INVENTION

The invention generally is directed to a releasably securable device for delivering oxygen to a wound or injury.

As used herein, the "terminals" of the power sources or batteries mean the parts or surfaces of the power sources or batteries to which external electric circuits are connected. Also, as used herein, the phrases "electrically connected" or "in electrical communication" or "electrically contacted" mean certain parts are in communication with each other by flow of electrons through conductors, as opposed to electrochemical communication which involves flow of ions, such as H+, through electrolytes.

Figure 1A:
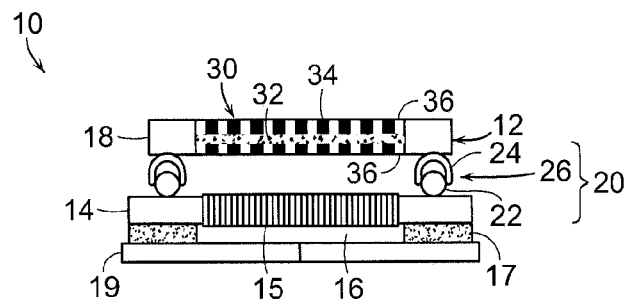
FIG. 1A is a cross-sectional view of one embodiment of a device for delivering oxygen of the invention.

FIG. 1A is a cross-sectional view of one embodiment of a device for delivering oxygen of the invention. Oxygen delivery device 10 includes bandage 12, which includes base 14 defining opening 16. Also included is cover 18 and locking mechanism 20 for releasably securing the cover to the base. Oxygen source 30 is in fluid communication with the cover, whereby oxygen is delivered to opening 16 in base 14.

Locking mechanism 20 includes interference-type fitting 26, such as a zip lock fitting or closure. As shown in FIG. 1A, interference-type fitting 26 typically includes male portion 22 and female portion 24. Male portion 22 can be attached to base 14 of bandage 12 and female portion 24 to cover 18 of bandage 12, or vice versa. The closure need not be continuous, but making it so allows locking mechanism 30 to close more securely and to provide a seal at the point of closure. Preferably, locking mechanism 20 is a continuous closure that provides a gas tight seal at the point of closure. Optionally, or alternatively, locking mechanism 20 includes an adhesive. The adhesive of the locking mechanism should be strong enough to hold the cover in place, but not so strong as to render separation of the cover from the base difficult without concurrent removal of bandage 12 from the wound site. Optionally, or alternatively, locking mechanism 20 may include a hook-and-loop fastener, such as a fastener made using Velcro® brand fabric or similar fastening material, that releasably secures the cover to the base.

Base 14 includes porous component 15 that conducts oxygen from oxygen source 30 to the wound or injury (not shown). As shown in FIG. 1A, porous component 15 is inside opening 16 of base 14. Preferably, base 14 includes adhesive layer 17, whereby bandage 12 can be fixed to skin around the wound or to a surface of a conventional bandage applied over the wound. Typically, adhesive layer 17 is covered by release paper 19 that is removed prior to application of bandage 12 to the skin or to a conventional bandage.

Preferably, as shown in FIG. 1A, adhesive strip 17 is attached to a perimeter of an underside of base 14 of bandage 12. Opening 16 in base 14 will provide a cavity between cover 18, including oxygen source 30, and the surface of the skin. The oxygen pressure in the cavity will vary depending on the size of the cavity as well as the size of the openings in cover 18 as well as the rate of oxygen production at source 30. Preferably, the pressure will not be so high so as to cause vasoconstriction.

Bandage 12, FIG. 1A, may have multiple layers to promote patient comfort and healing, including but not limited to layers of cotton gauze, polyethylene oxide-water polymer, as well as layer(s) containing topical ointments and other medicinals including antibiotics, antiseptics, growth factors and living cells. Preferably, bandage 12 is occlusive on all sides, except for opening 16 in base 14 and openings 36 in cover 18, to enable the maintenance of an oxygen rich atmosphere in the vicinity of the wound or injury.

Figure 1B:
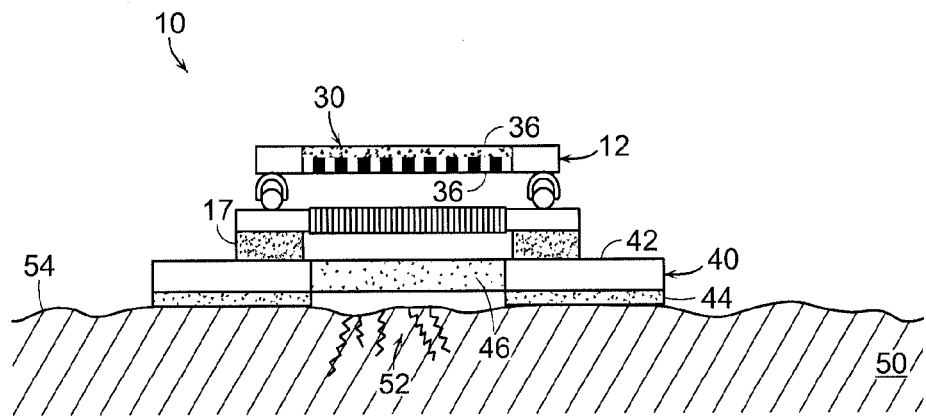
FIG. 1B is cross-sectional view of the device of FIG. 1A placed on top of a conventional bandage.

FIG. 1B is cross-sectional view of device 10 of FIG. 1A placed on top of conventional bandage 40 affixed to the surface of skin 50 surrounding wound 52. Conventional bandage 40 includes top surface 42, adhesive surface 44, and porous center 46. Typically, conventional bandage 40 is placed over a wound or injury before device 10 is applied to bandage 40. Conventional bandage 40 may be a commercially available wound dressing that is porous enough to allow the diffusion of oxygen through the dressing to the wound. As shown in FIG. 1B, bandage 40 is fixed to surface 54 of skin 50 surrounding wound 52 via adhesive surface 44. Preferably, porous center 46 of bandage 40 is located over wound 52. Typically, conventionally bandage 40 is placed over wound 52 first. Then, bandage 12 is placed on top of conventional bandage 40 such that adhesive layer 17 affixes base 14 of device 10 to surface 42 of bandage 40. Porous center 46 of conventional bandage 40 allows oxygen produced by oxygen source 30 to enter wound bed of wound 52. In one embodiment, a composite bandage is pre-fabricated from conventional absorbent bandage 40 and an oxygen generating device, such as oxygen delivery device 10, and applied to surface 54 of skin 50 surrounding wound 52.

Figure 1E:
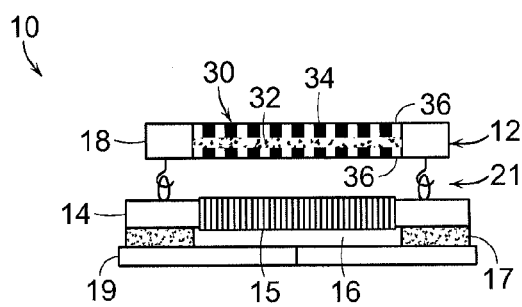
FIG. 1E is a cross-sectional view of another embodiment of the device, wherein the locking mechanism includes a hook-and-loop fastener.
Figure 1C:
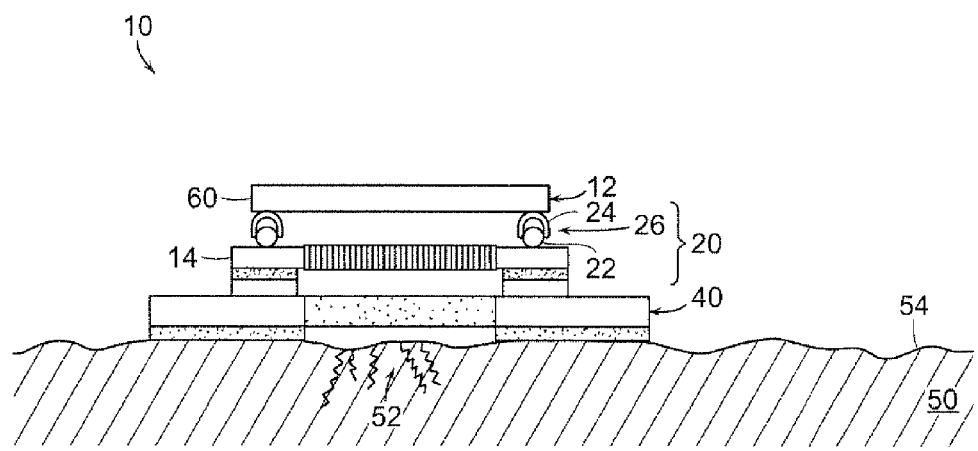
FIG. 1C is a cross-sectional view of the device of FIG. 1A, wherein the cover has been removed and replaced with a water-resistant blank.

FIG. 1C is a cross-sectional view device 10 of FIGS. 1A and 1B, wherein cover 18 has been removed and replaced with water-resistant blank 60. Although shown being placed over conventional bandage 40 in FIG. 1C, device 10 can be placed directly on top of skin 50. Locking mechanism 20 releasably secures blank 60 to base 14 in the same way locking mechanism 20 releasably secures cover 18 to base 14, as described above with reference to FIG. 1A. As shown in FIG. 1C, if locking mechanism 20 is interference-type fitting 26, male portion 22 of interference-type fitting 26 can be attached to base 14 of bandage 12 and female portion 24 to blank 60. Water-resistant blank 60, alone or in combination with a gas tight seal provided by locking mechanism 20, prevents water from entering bandage 12, thereby keeping wound 52 essentially sealed from outside water or other source of contamination.

Referring back to FIG. 1A, oxygen source 30 is preferably at cover 18 and may include a cathode and an anode that generate concentrated oxygen from ambient air by an electrochemical process. In one embodiment, oxygen source 30 is sealed into cover 18. Preferably, cover 18 defines openings 36 that provide fluid communication with ambient air, and that provide fluid communication between oxygen source 30 and wound or injury 52, as shown in FIG. 1B.

As shown in FIG. 1A, device 10 typically includes power source 34 that drives oxygen source 30. Power source 34 may be incorporated into or may be remote from bandage 12. Power source 34 may include a battery, such as a zinc-air battery or a lithium-ion battery and may include control circuitry. Optionally, the polarity of power source 34 is reversible to thereby modulate the oxygen concentration. In addition, power source 34 may apply a current to the oxygen source 30. The current may be adjustable to thereby modulate the oxygen concentration.

Figure 1D:
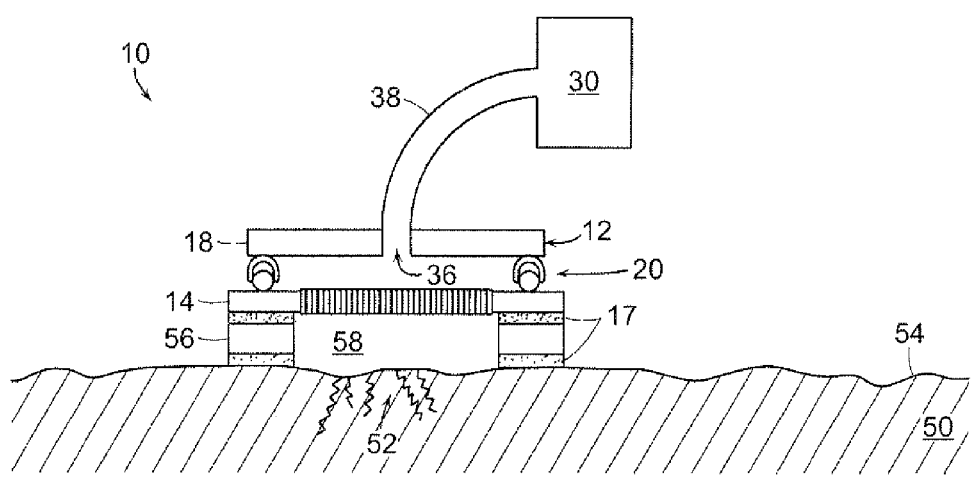
FIG. 1D is a cross-sectional view of one embodiment of a device for delivering oxygen of the invention, wherein the oxygen source is remote from the cover.

As shown in FIG. 1D, an embodiment of oxygen delivery device 10 includes oxygen source 30 remote from cover 18. Oxygen source 30 is in fluid communication with cover 18 through conduit 38. Preferably, conduit 38 is a flexible tubing fluidly connecting the oxygen source 30 with cover 18 of bandage 12. Cover 18, in turn is in fluid communication with underlying wound 52, for example, through openings 36. The flexible tubing may include a Luer type connection or similar type. The tubing is preferably made from a polymeric material suitable for use in hospital applications. Suitable materials for use in the tubing include, but are not limited to, silicone, polyethylene, polypropylene, polyurethane and various other thermoplastics.

Furthermore, oxygen delivery device 10 may include stand-off 56 on the bottom side of bandage 12, so as to form a pocket or cavity 58. For example, stand-off 56 may be formed integrally with base 14 or may be a separate component that is attached to the base. Optionally, or alternatively, stand-off 56 may be releasably secured to the underside of base 14. As shown in FIG. 1D, adhesive layer 17 attaches stand-off 56 to surface 54 or skin 50. Optionally, a second adhesive layer 17 attaches stand-off 56 to base 14. In some embodiments, adhesive layer 17 may be formed to create a stand-off, such as stand-off 56. Stand-off 56 is useful for those wounds which are superficial, e.g., venous leg ulcers. Most wounds have a depth, and oxygen reach into the wound is not a problem. However, venous ulcers are superficial wounds and compression dressings commonly used to treat venous ulcers sits on tightly on the wound. Stand-off 56 creates a small plenum, such as cavity 58, between a bandage, such as bandage 12, and the wound site for collection and concentration of oxygen directly over wound 52. Without a stand-off, there is a tendency in certain wounds, such as venous ulcers, for oxygen flow to follow a path of least resistance. Also, venous wounds are large in area, and it is imperative that the entire wound be draped with oxygen.

FIG. 1E is a cross-sectional view of another embodiment of the invention wherein the locking mechanism includes a hook-an-loop fastener 21.

FIG. 2A is a top view of bandage base 14 of one embodiment of oxygen delivery device 10 of the invention. Bandage base 14 defines opening 16 and includes porous element 15 covering opening 16. Bandage base 14 also includes male portion 22 of interference type locking mechanism 20.

FIG. 2B is a bottom view of bandage cover 18 of oxygen delivery device 10 of FIG. 1A. Bandage cover 18 includes female portion 24 of interference type locking mechanism 20. Cover 18 of the bandage includes oxygen source 30 in fluid communication with cover 18. As shown in FIG. 2B, oxygen source 30 includes membrane-electrode assembly (MEA) 32 electrically connected to power source 34. Cover 18 may also include control electronics. In some embodiments, the components of oxygen source 30 are sealed into removable cover 18 with openings only to allow air entry and oxygen exit. The openings may be holes or may be pores in a porous membrane. Preferably, air enters at the top surface of cover 18 and oxygen exits at the bottom surface of cover 18. The membrane may be selectively permeable to oxygen. Cover 18 may include different types of openings on the underside of cover 18 than on the top.

At least one advantage of the oxygen delivery device 10 with releasable oxygen source 30 is that the device can be applied over the wound as a unit, but individual components of the device, such as the bandage cover and the bandage base, are separable from one another, thereby allowing replacement of parts of the device without having to replace the entire device. For example, removable cover 18 of bandage 12 holds oxygen source 30, such as the EPIFLO® transdermal continuous oxygen therapy device, which includes a membrane-electrode assembly, a power supply, and, optionally, control electronics. The components of the oxygen source, including a power supply and any control electronics, are sealed into removable cover 18 with openings only to allow air entry and oxygen exit. In the case where battery 34 powers oxygen source 30, as for example shown in FIG. 2B, an exhausted battery or oxygen source can easily be replaced with a fresh battery or oxygen source, respectively, without the need to replace the entire bandage or the complete device. In this way, a patient's wound does not experience the stress associated with removing the adhesive part of the bandage each time the battery or the oxygen source is replaced.

Another benefit of locking mechanism 20 of the invention is that it releasably secures bandage cover 18 to bandage base 14, thereby allowing a doctor to easily remove cover 18 at any point to inspect the patient's wound or to refresh absorbents used in the bandage. Cover 18 may include oxygen source 30 and power source 34 and may be reused with the same or a different base 14. For example, power source 34 connected to oxygen source 30 may be a battery. After removal of cover 18 for inspection of the wound or replacement of bandage base 14, power source 34 may still have battery life remaining and both battery and oxygen source can be returned to bandage 12, thereby providing cost savings over conventional designs, where the bandage and the oxygen source, including the battery, are an integral unit. An additional benefit is that the patient can remove cover 18, including oxygen source 30 and battery 34, from bandage base 14 before bathing and resecure it to base 14 afterwards. A watertight blank 60, FIG. 1C, can be substituted for cover 18 while the patient is bathing, thereby keeping the wound dry.

Figure 3B:
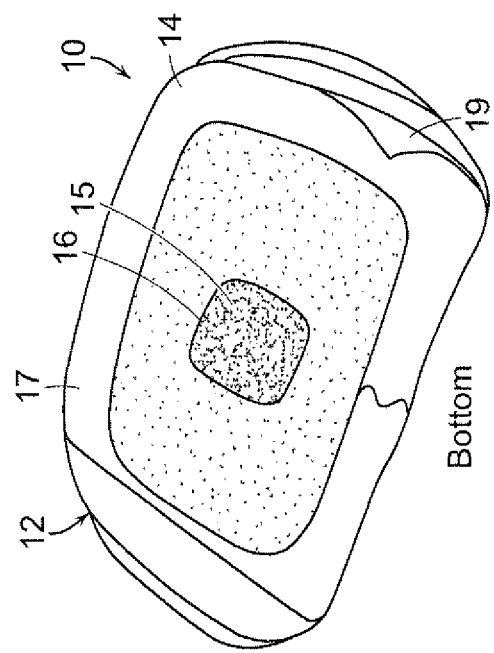
FIGS. 3A and 3B are top and bottom views, respectively, of an embodiment of an oxygen delivery device of the invention.
Figure 3A:
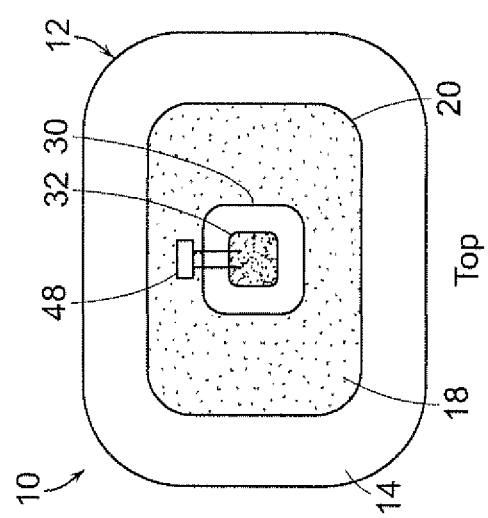

FIGS. 3A and 3B are top and bottom views, respectively, of an embodiment of an oxygen delivery device of the invention in which the power source is remote from the bandage. Oxygen delivery device 10 includes bandage 12, which includes base 14 defining opening 16, cover 18, and locking mechanism 20 for releasably securing the cover to the base. Oxygen source 30 is in fluid communication with the cover, whereby oxygen is delivered to the opening in the base. As shown in FIG. 3A, oxygen source 30 includes membrane electrode assembly 32 and connector 48 for electrically connecting oxygen source 30 to a remote power supply (not shown). Connector 48 is preferably located on the top side of bandage 12 for easy access by a doctor or a patient.

Locking mechanism 20 may include an interference-type fitting, such as fitting 26 described above with reference to FIG. 1A. As shown in FIG. 3B, base 14 includes porous component 15 that conducts oxygen from oxygen source 30 to the wound or injury (not shown). Porous component 15 may be inside opening 16 of base 14. Preferably, base 14 includes adhesive layer 17, whereby bandage 12 can be fixed to skin around the wound or to a surface of a conventional bandage applied over the wound. As shown in FIG. 3B, adhesive layer 17 is typically covered by release paper 19 prior to application of bandage 12 over the wound.

Figure 4A:
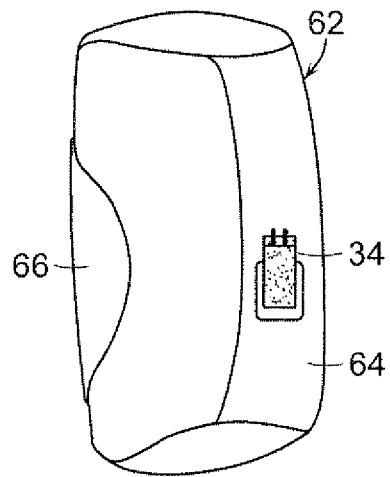
FIG. 4A is a perspective view of one embodiment of a holster for holding a power source of the oxygen delivery device of FIG. 3A.

FIG. 4A is a perspective view of one embodiment of holster 62 for holding power source 34 of oxygen delivery device 10 of FIG. 3A. Holster 62 includes a component 64 for mounting the holster on a patient. Component 64 may be an elastic bandage that can wrap around and conform to a patient's limb, such as an ACE® brand elastic bandage, thereby holding holster 62 in place. Component 64 my be collapsible elastomeric stockings with a pouch holding power source 34, including a battery and control circuit, for use with oxygen generating device 10 shown in FIGS. 3A-3B. In some embodiments, component 64 allows mounting of holster 62 at or near a wound or skin injury, in which case it may also include opening 66 to allow access to the wound or injury. Opening 66 is preferably sized to allow placement of bandage 12 over the wound without interference by holster 62.

Figure 4B:
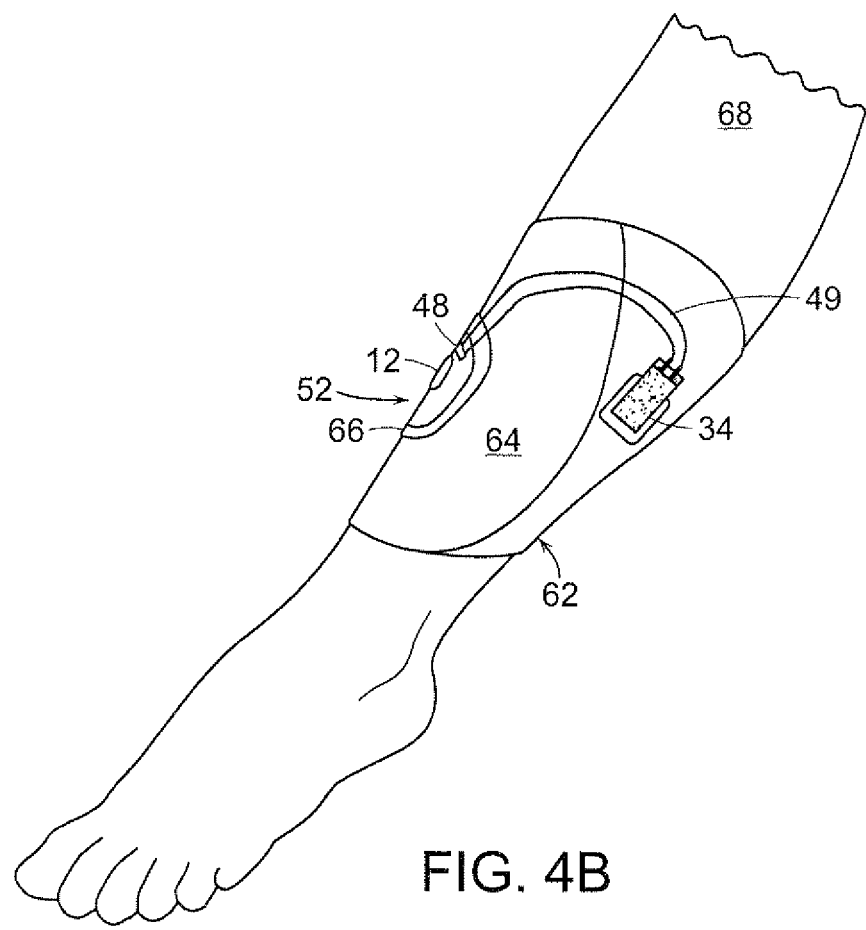
FIG. 4B is a schematic view of the holster of FIG. 4A mounted on a limb of a patient.

FIG. 4B is a schematic view of holster 62 of FIG. 4A mounted on limb 68 of a patient. Bandage 12 of oxygen delivery device 10 of FIGS. 3A-3B is placed over wound 52 and connector 48 is electrically connected to the terminals of power source 34 via leads 49. Holster 62 holds power source 34 remote from wound 52. Preferably, power source 34 includes a battery. Power source 34 may also include control circuitry.

As described above, device 10 will preferably use one or more batteries as a power source. The device may also include a circuit board. The circuit board may have an electronic timing device that can be set for a defined period of oxygen delivery, such as a seven-day or 15-day oxygen therapy treatment. Embodiments of the oxygen delivery device of the invention, such as device 10 shown in FIGS. 1A-1B, may be powered by a variety of primary or secondary battery power sources, including alkaline manganese-dioxide, zinc-air, lithium thionyl chloride, lithium manganese dioxide, lithium ion, nickel metal hydride and the like.

In one embodiment, the device includes a remote power source that can be positioned on the patient wherever convenient and comfortable. Patients with wounds on the bottom of their feet, for example, can wear a thin bandage, connect the flexible leads of the power source to the oxygen source, and attach the power source away from the wound on the ankle or leg. For example, patients can place the power source in a holster that includes a component for mounting the holster on patient's limb. The patient is thus able to wear a shoe while being treated with oxygen without having size and comfort restraints created by the prior art. For patients with wounds to the sacrum, heel, back or other pressure points, the power source can be remotely placed away from the wound and pressure point for optimum comfort. Then, the relatively flexible leads can be directed to the wound site.

An oxygen source for use in embodiments of the present invention may operate based on similar principles as those described in U.S. Pat. No. 5,578,022, (incorporated herein by reference in its entirety) which has been commercialized by Ogenix Corporation under the name EPIFLO®, and cleared by the FDA for the treatment of certain types of wounds. More specifically, it uses oxygen reduction at a high area gas permeable cathode yielding water as a product, and water oxidation at a high area gas permeable anode to generate pure oxygen. Both electrodes are attached to opposite surfaces of a thin polymer electrolyte membrane (PEM), e.g., NAFION® perfluorinated polymer membrane containing small proportions of sulfonic or carboxylic ionic functional groups, in much the same way as in PEM fuel cells. The anode and cathode sides of the cell are isolated from each other. As the gas permeability of the assembly is very low, operation of the device enriches the oxygen content of the side facing the anode, and, at the same time, depletes the oxygen content of the side facing the cathode.

Figure 5:
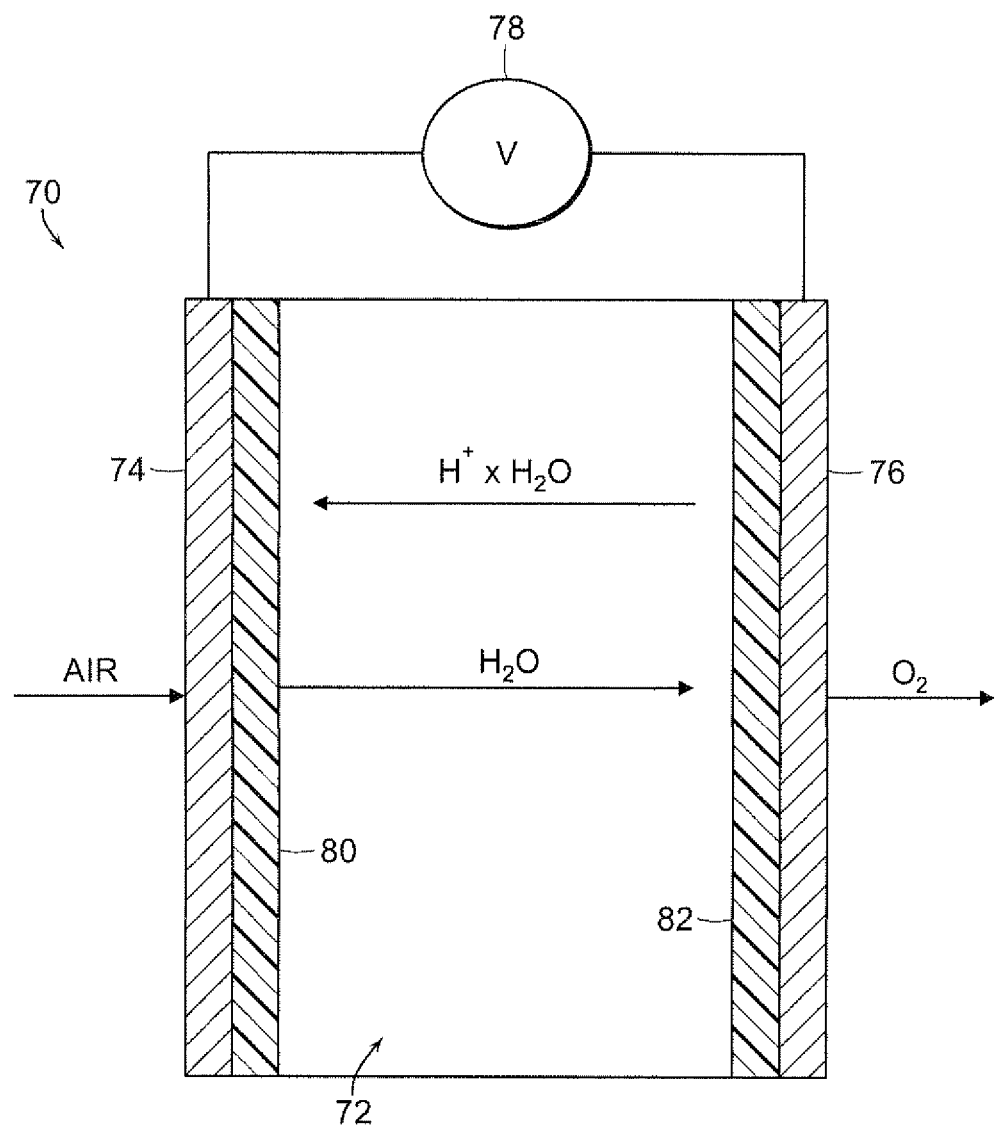
FIG. 5 is a schematic diagram of a membrane electrode assembly for use in the present embodiments.

With reference to FIG. 5, an oxygen source, such as oxygen source 30 of FIGS. 1A, 1B and 1D, suitable for use in any of the above described embodiments can be described generally as comprising a membrane electrode assembly (MEA) or electrochemical cell 70 for the electrochemical concentration of oxygen from air. An ion conducting membrane 72 is positioned between two electrodes 74, 76, which in turn are electrically connected to a power source 78, such as a battery, capable of passing a current across the electrodes.

As shown in FIG. 5, oxygen in ambient air is reduced to water at an interface region 80 between the cathode 74 held at a reducing potential and the membrane 72 using the protons supplied by the membrane according to a reaction as described below. The product water migrates (or diffuses) through the membrane 72 to the anode 76 held at an anodic potential, which oxidizes the water back to oxygen while releasing protons at an interface region 82 between the anode and the membrane. The protons move through the membrane to the cathode 74 to make possible continued reduction of oxygen from air. Atmospheric nitrogen and carbon dioxide are electrochemically inert under the reaction conditions required for oxygen reduction and, thus, are effectively rejected at cathode 74. The reduction product of oxygen alone moves through membrane 72, resulting in near 100% pure oxygen on anode 76. This oxygen is then available for delivery to a wound site.

Thus, the following reaction mechanisms may be used in the present invention for the production of oxygen:

At the cathode: $O_2 + 4H^+ + 4e^- \rightarrow 2H_2O$

At the anode: $2H_2O \rightarrow O_2 + 4H^+ + 4e^-$ with the net reaction being the depletion of a gaseous oxygen (from ambient air) on the cathode side of the membrane and an increase of the oxygen concentration on the anode side in fluid communication with a wound site.

The ion conducting membrane may be any of a number of known ion conducting membranes which are capable of conducting protons and other ionic species. Suitable membranes include various perfluoronated ionomer membranes that include a poly(tetrafluoroethylene) backbone and regularly spaced perfluoronated polyether side chains terminating in strongly hydrophilic acid groups. A preferred group of membranes suitable for use in the present invention include those containing sulfonic acid terminating groups on the side chains and available under the trademark NAFION® from E. I. Dupont Co. NAFION® is a perfluorinated polymer that contains small proportions of sulfonic or carboxylic ionic functional groups. Its general chemical structure can be seen below, where X is either a sulfonic or carboxylic functional group and M is either a metal cation in the neutralized form or an $H^+$ in the acid form. Other suitable membranes include partially fluorinated membrane materials and those based on hydrocarbon polymer backbones.

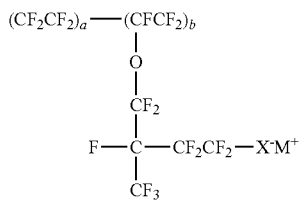

In one embodiment of the present invention, a NAFION® membrane is treated or imbibed with 85-100% phosphoric acid. In NAFION®, water normally provides the hydrogen bonding network and enables the rapid movement of protons through the polymer (and hence the high ionic conductivity). However, when left under ambient conditions, NAFION® loses water to the surroundings (due to the relatively high vapor pressure of water), which results in the loss of ionic conductivity. Phosphoric acid can also provide a hydrogen bonding network similar to that of water, but unlike water, has a very low vapor pressure—at room temperature the vapor pressure of phosphoric acid is so low that it can be considered zero. It is also hygroscopic to a degree, such that it may absorb water from the atmosphere. This combination of properties makes it possible to replace most of the water in NAFION® with phosphoric acid under appropriate conditions.

The electrodes used in the membrane electrode assembly can be in the form of a mesh or a thin coating on the opposite surfaces of the membrane. They can be made of any materials which are electrically conductive and which will catalyze the reduction of gaseous oxygen into water, and catalyze the oxidation of the product water to release oxygen. Suitable electrode materials include, but are not limited to, platinum, iridium, rhodium, ruthenium as well as their alloys and oxides in a pure finely divided form or as supported catalysts.

A method of making a membrane electrode assembly that is capable of accomplishing the above goal consists of bonding a Pt/C electrode and a Pt black electrode to either side of a NAFION® 117 (or similar) membrane. The electrical connections from the electrodes to the voltage source are normally provided through conducting end plates that are normally made of thick graphite or metallic material. To reduce weight and improve mobility of the device, a thin (e.g., 1-5 mil), electronically conducting and electrochemically inert wire is placed in between the membrane and electrode during the bonding process, thereby making the electrical connection an integral part of the membrane electrode assembly. Examples of such wires include: gold, Pt, gold or Pt plated or deposited Ta, and similar materials.

In addition, a catalyst may be used to improve the electrochemical production of oxygen in the above reactions. The addition of a catalyst in one or both electrodes aids in overcoming the kinetic reaction barriers. Preferably, a Pt—Ru, Pt—Ir, or similar noble metal alloy catalyst that is poison resistant is used to coat the electrodes. The use of such poison resistant catalysts will prevent impurities introduced from the adhesive and other components of the device from reducing the catalyst activity and deactivating the device. Suitable non-limiting examples of anode catalysts include Pt—Ir, Pt—Sn, and ternary combinations thereof. Anode catalysts may also include ternary compositions of Pt, Ir, Sn and a valve metal. Valve metals include Al, W, Ti, Ta, Hf, Nb, and Zr. Suitable non-limiting examples of cathode catalysts include Pt, Pt—Ru/C, Pt—Sn, Pt—Ir, Pt—C, and ternary combinations thereof. Cathode catalysts may also include ternary compositions of Pt, Ir, Ru, Sn and a valve metal, either as a metal or alloy black or as deposited on a carbon substrate. A preferred catalyst for both the anode and the cathode is Pt—Ir.

The electronic circuit board or controller may contain an on-off switch and a current monitoring port. The amount of oxygen generated by the device can be varied by changing the voltage applied across the electrodes or by modulating the current delivered to the electrodes. Typically, the device will produce between about 0.1 and about 50 ml oxygen/hr, under standard temperature and pressure, more preferably between about 1 and about 10 ml/hr.

In another embodiment, the invention is a method for treating a wound with oxygen gas. The method includes applying a bandage to a wound site. The bandage includes a base defining an opening, a cover and a locking mechanism for releasably securing the cover to the base. An oxygen source that is in fluid communication with the cover is actuated, and oxygen gas is delivered from the oxygen source through the cover to the opening in the base thereby treating the wound with oxygen gas.

Embodiments of the present invention may be considered universal oxygen delivery devices having a releasable oxygen source in that they can be used with a wide variety of bandages or dressings already on the market. Additional types of dressings with which embodiments of the present invention may be used include fully occlusive thin film dressings, hydrocolloid dressings, alginate dressings, antimicrobial dressings, biosynthetic dressings, collagen dressings, foam dressings, composite dressings, hydrogel dressings, warm up dressings, and transparent dressings.

In other applications, the device is capable of treating venous leg ulcers where the patient must wear woven four part compression dressings to control swelling and edema. The oxygen producing device can be placed on the top layer of the compression dressing, thus avoiding compressing the device tightly against the leg as would be necessary with prior art devices. Alternatively, the bandage of the oxygen delivery device may be placed between the four individual layers of the compression dressing to conform directly to the leg without unduly compressing the oxygen source, batteries and hardware comprising the oxygen producing device against fragile skin surrounding the wound. Positioning the oxygen delivering bandage on top of the compression dressing also provides the further advantage of assuring unrestricted delivery of oxygen from atmospheric air to the wound, rather than relying on atmospheric diffusion through the dressing.

While this invention has been particularly shown and described with references to example embodiments thereof, it will be understood by those skilled in the art that various changes in form and details may be made therein without departing from the scope of the invention encompassed by the appended claims.

What is claimed is:

1. A device for delivering oxygen to a wound or injury, the device comprising:
   a) a bandage, including,
      i) a base defining an opening,
      ii) a cover wherein the cover defines openings that provide fluid communication with ambient air,
      iii) a locking mechanism for releasably securing the cover to one side of the base, wherein the locking mechanism includes an interference-type fitting having a male portion and a female portion, the male portion being attached to one of the base and the cover, the female portion being attached to the other of the base and the cover, and includes a continuous closure that provides a gas-tight seal at the point of closure, and
      iv) an adhesive at a perimeter of an opposite side of the base;
   b) an oxygen source sealed into the cover that includes a cathode and an anode that generate concentrated oxygen from ambient air by an electrochemical process, whereby the concentrated oxygen from the oxygen source is delivered to the opening in the base; and
   c) a battery incorporated into the cover.

2. The device of claim 1, further including a water-resistant blank, whereby the cover can be removed and replaced with the water-resistant blank, thereby keeping the wound dry.

3. The device of claim 1, wherein the base further includes a porous component that conducts oxygen from the oxygen source to the wound or injury.

4. The device of claim 1, wherein the battery includes a primary battery.

5. The device of claim 1, wherein the battery includes a rechargeable battery.

6. The device of claim 1, wherein the polarity of the battery is reversible, to thereby modulate the oxygen concentration.

7. The device of claim 1, wherein the oxygen source further includes a phosphoric acid-treated ion conducting membrane.

8. The device of claim 7, wherein the oxygen source generates oxygen according to a four-electron process.

9. The device of claim 7, wherein said ion conducting membrane is a perfluorinated ionomeric membrane.

10. The device of claim 7, wherein said battery applies a current across said cathode and anode.

11. The device of claim 7, further including a catalyst in at least one of said anode and cathode.

12. The device of claim 11, wherein said catalyst on the cathode comprises Pt, Pt—Ru, Pt—Sn, Pt—Ir or ternary compositions of Pt, Ir, Ru, Sn and a valve metal, either as a metal or alloy black or as deposited on a carbon substrate, and said catalyst on the anode comprises Pt—Ir, Pt—Sn, or ternary compositions of Pt, Ir, Sn and a valve metal.

13. The device of claim 7, wherein said device generates between about 0.1 to about 50 ml oxygen/hr under standard temperature and pressure.

14. The device of claim 1, wherein the battery applies a current to the oxygen source, said current being adjustable, to thereby modulate the oxygen concentration.

15. The device of claim 1, wherein the bandage further includes medicinal components.

16. The device of claim 1, wherein the base further includes a stand-off that creates a plenum between the bandage and the wound for collection and concentration of oxygen directly over the wound.

17. A method for treating a wound with oxygen gas, comprising the steps of:
   a) applying a bandage to a wound site, the bandage including,
      i) a base defining an opening,
      a cover wherein the cover defines openings that provide fluid communication with ambient air,
      iii) a locking mechanism for releasably securing the cover to one side of the base, wherein the locking mechanism includes an interference-type fitting having a male portion and a female portion, the male portion being attached to one of the base and the cover, the female portion being attached to the other of the base and the cover, and includes a continuous closure that provides a gas-tight seal at the point of closure, and
      iv) an adhesive at a perimeter of an opposite side of the base;
   b) actuating an oxygen source sealed into the cover by actuating a battery incorporated into the cover; and
   c) delivering oxygen from the oxygen source through the cover to the opening in the base, thereby treating the wound with oxygen gas.

18. The method of claim 17, further including the steps of removing the cover, changing the bandage base, and replacing the cover.

19. The method of claim 18, wherein the cover is replaced with a water-resistant blank.

* * * * *

UNITED STATES PATENT AND TRADEMARK OFFICE
CERTIFICATE OF CORRECTION

PATENT NO. : 8,439,860 B2
APPLICATION NO. : 12/709902
DATED : May 14, 2013
INVENTOR(S) : Lawrence J. Cali, Srinivasan Sarangapani and Jeffrey C. DiTullio It is certified that error appears in the above-identified patent and that said Letters Patent is hereby corrected as shown below:

In the Claims:

In Column 12, Claim 17, Line 24, insert --ii)-- in front of "a cover"

Signed and Sealed this
Sixteenth Day of July, 2013

Teresa Stanek Rea
*Acting Director of the United States Patent and Trademark Office*